US012607641B2

(12) United States Patent
Cohen et al.

(10) Patent No.: US 12,607,641 B2
(45) Date of Patent: ***Apr. 21, 2026

(54) APPARATUS AND METHOD TO DETERMINE STROKE SUBTYPE

(71) Applicant: Haemonetics Corporation, Boston, MA (US)

(72) Inventors: Eli Cohen, Skokie, IL (US); Gabriel Raviv, Glenview, IL (US); Irene Navickas, Hauula, HI (US)

(73) Assignee: Haemonetics Corporation, Boston, MA (US)

( * ) Notice: Subject to any disclaimer, the term of this patent is extended or adjusted under 35 U.S.C. 154(b) by 1131 days.

This patent is subject to a terminal disclaimer.

(21) Appl. No.: 15/526,757

(22) PCT Filed: Nov. 13, 2015

(86) PCT No.: PCT/US2015/060499
§ 371 (c)(1),
(2) Date: May 14, 2017

(87) PCT Pub. No.: WO2016/077657
PCT Pub. Date: May 19, 2016

(65) Prior Publication Data
US 2018/0238913 A1     Aug. 23, 2018

(51) Int. Cl.
*G01N 33/86*       (2006.01)
*A61B 5/15*        (2006.01)

*C12Q 1/56*        (2006.01)
*G01N 33/68*       (2006.01)

(52) U.S. Cl.
CPC ....... *G01N 33/86* (2013.01); *A61B 5/150755* (2013.01); *C12Q 1/56* (2013.01); *G01N 33/6893* (2013.01); *G01N 2333/974* (2013.01); *G01N 2800/224* (2013.01); *G01N 2800/2871* (2013.01)

(58) Field of Classification Search
CPC .............. G01N 33/86; G01N 33/6893; G01N 2800/224; G01N 2333/974; G01N 2800/2871; G01N 29/036; C12Q 1/56; A61B 5/150755
See application file for complete search history.

(56) References Cited

U.S. PATENT DOCUMENTS

| | | | | |
|---|---|---|---|---|
| 9,068,966 B2 * | 6/2015 | Delmenico | ........ | G01N 33/4905 |
| 2011/0117586 A1 * | 5/2011 | Cohen | .................... | G01N 33/86 |
| | | | | 435/13 |
| 2014/0328732 A1 * | 11/2014 | Delmenico | ......... | B01L 3/50273 |
| | | | | 422/537 |

* cited by examiner

*Primary Examiner* — Dennis White

(57)          ABSTRACT

Apparatus and methods are provided to determine stroke subtype by hemostasis measurement at point of care or first response. A testing apparatus and methods may provide first test to determine an ischemic or hemorrhagic indication and a second test to provide a therapeutic influence before classifying a stroke subtype.

10 Claims, 4 Drawing Sheets

APPARATUS AND METHOD TO DETERMINE STROKE SUBTYPE

CROSS-REFERENCE TO RELATED APPLICATION

This patent claims priority to U.S. Provisional Patent Application Ser. No. 62/079,631 filed Nov. 14, 2014, the disclosure of which is hereby expressly incorporated herein by reference.

TECHNICAL FIELD

This patent relates to technology to classify strike subtype as hemorrhagic or ischemic by selectively transforming a whole blood sample.

BACKGROUND

Stroke is one of the leading causes of death and serious, long-term disability in the United States, which means nearly 900,000 people suffer a new or recurrent stroke each year, and someone dies of a stroke every four minutes. An urgent need is to distinguish ischemic (blood clot) from hemorrhagic (bleeding) stroke subtypes more rapidly to accelerate the start of ischemic or hemorrhagic stroke therapy. Each requires a totally different therapy—the wrong therapy can be fatal. The purpose of ischemic stroke therapy is to dissolve the clot, usually with thrombolytic drugs such as TPA, while hemorrhagic stroke therapy is to enhance clot formation to stop bleeding, using transfusions of platelets, FFP, fibrinogen concentrates, and rFVIIa.

Stroke is the expression of a hemostasis disorder, generally either as an acute ischemic stroke caused by inappropriate clotting or as an intracerebral hemorrhage (ICH) with inappropriate bleeding. Despite this, hemostasis is largely ignored in the diagnosis and subsequent treatment of stroke.

It has been established that "earlier is better" when it comes to treatment. Hence there is a critical need to distinguish stroke subtype at the earliest possible time following indications of a stroke event. Yet, in spite of knowing of this problem and need, effective technology still does not exist to early distinguish stroke subtype.

DETAILED DESCRIPTION

Figure 1:
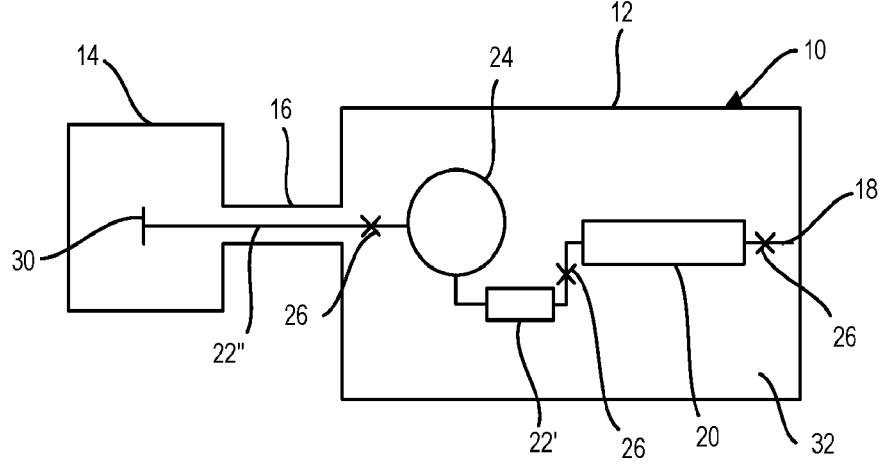
FIGS. 1 & 2 schematically illustrate a point-of-care hemostasis testing device that may be configured to provide an early stroke subtype determination.

Described herein is technology incorporating hemostatic measurement to provide the early identification of acute ischemic and hemorrhagic stroke. Transformative apparatus and associated operating methodologies transforms whole blood through thombelastography. This effective transformation yields hemostasis data and further enables the development of a Stroke Index. Preferably, the transformative apparatus includes suitably configured apparatus capable of measuring hemostasis. The hemostasis data may further and optionally be combined with related clinical indicators such as NIHSS scores along with other markers to facilitate treatment with fibrinolytic agents (e.g., rTPA) for ischemic stroke or clot-enhancing agents (e.g., platelets) for hemorrhagic stroke in selected patients, as well as monitoring response to such treatment.

The CORA® point-of-care hemostasis system, available from Coramed Technologies, LLC, Glenview, Ill., is able to provide the required transformative action upon whole blood samples and to create from such transformation critical hemostatic information that go well beyond the guideline-suggested INR/PTT testing, and well within the targeted 60 minute door-to-needle time, which is the critical time for mimimizing the debilitating effects of stroke. Therefore, the CORA® device may be configured and utilized in accordance with the herein described embodiments to provide an early stroke subtype determination.

The ability of the transformative apparatus, a whole-blood thrombelastography device, to provide a total picture of the hemostasis process from initial clot formation through final clot dissolution that also is able to identify both bleeding and thrombotic disorders differentiates thombelastography and in particular CORA® analysis technology from other coagulation tests. The CORA® technology, for example, using whole blood is capable of reporting an integrated net effect of all the factors that contribute to hemostasis in a single sample run.

In accordance with inventive embodiments herein described, and modifications and alterations of which as will be appreciated by the skilled person, provided is a point-of-care comprehensive global hemostasis analysis system with operative algorithms and stroke Index determination capability specifically targeted to provide stroke subtype determination. One outcome from early determination of stroke subtype is that, for the first time, it is possible to understand and use hemostais, the culprit in ischemic and hemorrhagic stroke, as a route to treat stroke. A clot, a simple mechanical structure, impedes or obstructs the flow of blood in the brain—an ischemic stroke. Blood with factor deficiencies, an excessive level of anticoagulation, and/or platelet inhibition can cause bleeding in the brain—a hemorrhagic stroke.

Although new platelet-based tests are emerging, most standard laboratory tests are still plasma-based and ignore the role of platelets and their interaction with coagulation proteins in patient hemostasis. Standard coagulation tests (PT, PTT, aPTT, etc.) end when only approximately 5% of thrombin has been formed. D-dimer testing measures fibrin degradation products and not true fibrinolysis, and cannot distinguish between primary and secondary fibrinolysis. Many other routinely-prescribed tests monitor the quantity of isolated components, but not the functionality and interaction of these components. Effective measurement of patient hemostasis requires a whole blood global hemostasis test, i.e., thrombelastography, to measure the net effect of all interactions.

The CORA® technology incorporates a novel measurement technique, in which the viscoelastic properties of a clot are determined by performing a series of non-contact measurements of the resonant frequency of a sample in response to external vibration. This approach has many benefits, one of which is that it gives coagulation measurements directly comparable to the widely accepted parameters from the TEG 5000 analyzer.

FIG. 1 graphically depicts a sample testing cartridge 10 that includes a sample processing portion 12, a sample retention portion 14 and a suspension, e.g., beam 16 structurally, mechanically joining the sample retention portion 14 to the processing portion 12. The beam 16 shown in a cantilever configuration allows the sample retention portion 14 to act as a sprung mass relative to the sample processing portion 12 and to vibrate in response to a stimulus applied to the cartridge 10. Other structures, such as spring, multi-link suspensions, a rigid or semi-rigid member or members and the like capable of mechanically joining while allowing relative, dynamic movement of the sample retention portion to the sample processing portion may be used. It will be appreciated relatively small displacement, i.e., vibration of the sample is required. In certain embodiments, it may be possible to directly join the processing portion 12 and the retention structure 14 even forming them as an integral member.

The sample processing portion 12 includes a port 18 through which a liquid sample 100 may be introduced into the sample processing portion 12. The port 18 may be self-sealing (as in a septum or other automatic sealing mechanism) such that the sample once introduced into the cartridge 10 does not flow, leak, seep, etc. from the cartridge. The port 18 communicates with a reservoir 20 into which the sample is initially received. The sample processing portion 12 additionally includes channels, via, waste chambers, passages and similar structures 22; a bellows or pump 24 and valves 26 to control movement of the sample 100 or a portion thereof through the sample processing portion 12 responsive to actuation of the bellows 24 to prepare the sample 100 for testing.

Pneumatic force, which can be applied pressure, drawn vacuum or combinations thereof, and in a preferred implementation is vacuum, may be used directly on the sample 100 to move it into the cartridge 10 and to manipulate the various elements of the cartridge 10. In the illustrated implementation, vacuum applied at a central port 19 causes the sample 100 to load into a staging area 20 and further draws the sample 100 into the bellows 24. The sample 100 is drawn up to the hydrophobic vents 28, allowing careful control of the sample fluid volumes solely with the card geometry. As such, it is unnecessary to monitor loading time or otherwise actively sense of the volume of the sample 100, simplifying the structure and operation of the cartridge 10.

Application of vacuum to the bellows 24 and operation of selected valves 26 causes the sample portion 100 to be drawn from the staging area 20 and through and into a first passage 22'. The first passage 22' may include a testing reagent, in liquid, gel, lyophilized, dried or other suitable form that is reconstituted by, and then mixed with the sample portion 100 as it is drawn into and through the passage 22'. Cycling of the bellows 24 provides mixing of the sample and reagent by repeated communication of the sample 100 into and through the first passage 22'. Control of the valve 26 and actuation of the bellows 24 then allows communication of the conditioned sample portion 100 through a second passage 22" to the sample retention structure 14.

Bellows 24 operation to communicate the sample portion 100 through the cartridge 10 is not limited to operating the bellows in a binary fashion. Applying pneumatic pressure and/or vacuum to the bellows 24 via predetermined profiles, for example ramps, arcs and the like, provides a very controlled approach to the fluid flow profile within the sample processing portion 12 to limit fluid shear in the passages 22 which can lead to sample activation and furthermore to avoid bubble formation. Pneumatic inputs to the cartridge 10 and the bellows 24 through a flow restriction outside the card filters out pulsations caused by pulse-width-modulation (PWM) operation of the solenoid valve controlling the bellows 24.

Reagent reconstitution and mixing with the sample 100 may be accomplished by locating the reagent or multiple reagents at various locations within the cartridge 10 and exposing the sample portion 100 to the reagents. Reagents may be positioned at virtually any other location: wells, passages, via, chambers, bellows, and sample retainers, within the cartridge 10 where the reagents will contact the sample portion 100. Reagents may further be placed in the sample containment structure 30. For example, heparinase may be placed in the staging area 20 or other sample reservoir area of the cartridge 10. The sample portion 100 may then be drawn into the staging area 20 and allowed to remain in contact with heparinase for sufficient time to reconstitute the dried heparinase and counteract sodium heparin in the sample 100. This is prior to the sample 100 being pulled into the bellows and flowing through a reagent well, i.e., passage 22', where the treated sample 100 will contact other reagents. Spot reagents may be applied virtually anywhere on the cartridge, and additionally, reagent may coat the sample containing structure 30. Thus it will be appreciated that a cartridge 10 in accordance with various embodiments of the invention may have numerous different reagents located at numerous different locations of the cartridge in virtually any set of combinations, and therefore that cartridge 10 is ideally suited for configuration in accordance with the herein described embodiments.

The sample retention structure 14 communicates with the second passage 22 and includes a containing structure 30 for holding or containing the sample portion 100 during testing of the sample portion 100. For example, the sample retention structure 14 may include an annulus, cylinder, cup, or similar containing structure 30 that provides a sample surface free to be excited to resonant or near-resonant vibration and observed by a sensing device. One containing structure 30 includes a containing wall leaving two surfaces of the sample free to be excited to resonant or near-resonant vibration. The sample may be introduced to the containing structure 14 via a side port extending through the containing wall. U.S. Pat. Nos. 9,066,968; 8,236,568; 7,879,615 and 7,261,861 describe several additional possible sample containing structures 30, which may be suitable structures for use in an embodiment of the cartridge 10.

Figure 2:
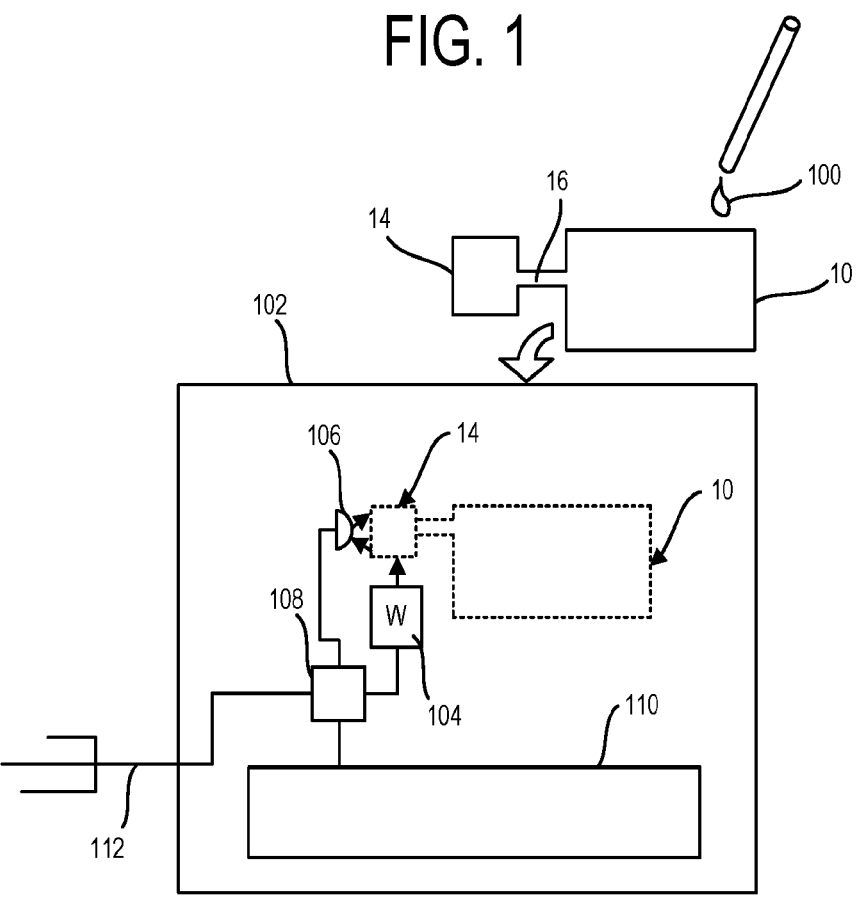

The cartridge 10 charged with a sample 100 is usable in an apparatus for measuring hemostasis 102. Depicted schematically in FIG. 2, the elements of the apparatus 102 are an exciter, shaker or similar stimulus generator 104, sensor/detector 106, processor 108, user interface 110 and communication link 112. A suitable power supply (not depicted) is provided. The exciter 104 can be a coil, piezoelectric device, motor, acoustic actuator or any suitable device to cause resonant excitation of the sample 100 within the sample retention apparatus 14 via direct stimulation of the retention apparatus 14 or indirectly via excitation of the cartridge 10 or a portion of the cartridge 10 or via combinations thereof. The sensor 106 may be an optical/laser device. The user interface 110 may be hard buttons, touch screen or any suitable interface to allow the user to select and initiate a testing protocol and to view or to affect recording or transmitting of the results. The processor 108 operably links these functional elements and facilitates communication by the communication link 112, which may be a wireless or wired network interface following any suitable protocol. For example, the communication link 112 may be used to communicate results data to a remote processing facility for analysis and diagnostic interpretation and to receive results analysis for display in data and graphic form via the user interface 110. The processor 108 furthermore may include or be provided with programming or program instructions executable by the processor to control operation of the apparatus 102 to affect transformation of sample material and to gather information relating to the sample during various stages of transformation.

The cartridge 10 is placed within the testing apparatus 102. The blood sample 100, such as fresh whole blood, blood components, and the like is introduced into a reservoir 18 within the cartridge 10 via the port 20. The apparatus 102 is configured to selectively apply pneumatic signals, such as drawing a vacuum at a selected position of surface 32 of the cartridge 10 or actuating valves within the cartridge 10, in a predetermined testing protocol to condition the sample portion 100 by mixing with reagent and then communicating it to the sample retention structure 14.

Figure 3:
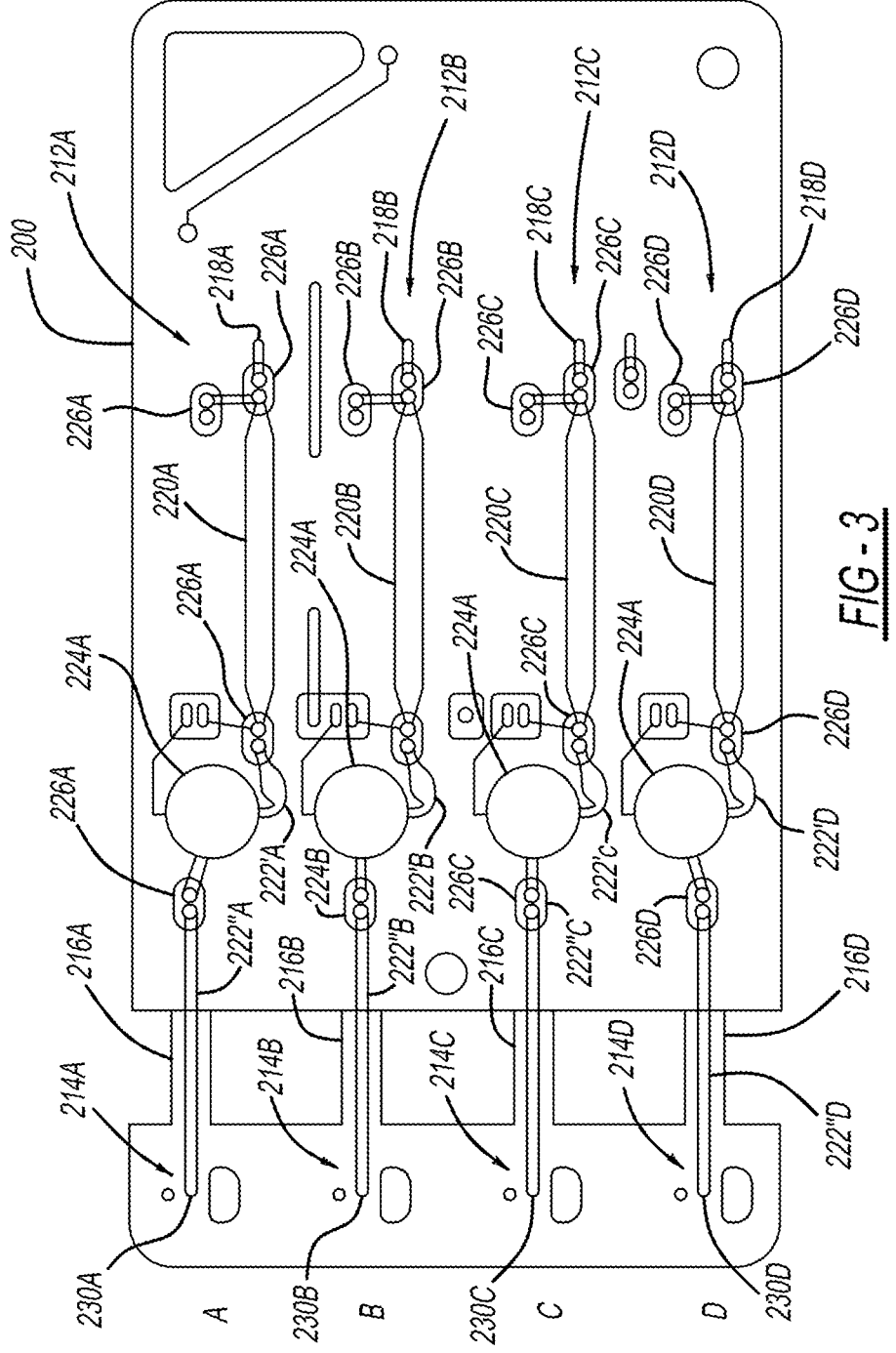
FIG. 3 is a graphic illustration of a testing cartridge configured for point-of-care stroke subtype determination and suitable for use with the device illustrated in FIGS. 1 & 2.

FIG. 3 graphically illustrates a cartridge 200 that may be used in sample testing, such as in hemostasis sample testing of a whole blood or blood component sample. The cartridge 200 has features similar to that of cartridge 10, but provides potential for multiple simultaneous tests. That is, each channel on the cartridge may contain different reagents and hence constitute different tests or may be configured to provide redundant tests. Each individual or combination of tests may constitute an assay. The cartridge 200 may be configured to provide up to four (4) tests simultaneously. Although, in use any combination from one (1) to four (4) tests may be performed. Cartridge 200 also demonstrates that a cartridge may be made with virtually any number of tests, with FIG. 1 and FIG. 3 demonstrating at least single test cartridges and four (4) test cartridges, cartridges of 2 or 3 tests may be made as well as cartridge having more than four (4) tests may be made. A channel or channels of the cartridge may be a test or tests to test a specific characteristic of hemostasis that may be used in an assay of such hemostasis related characteristics, such as platelet activity, ischemic risk indicators, or the like as set forth in the aforementioned US patents. The cartridges 200 may be configured to provide multiple tests or may be made to provide the same tests with multiple different samples, or combinations thereof.

As seen in FIG. 3, the cartridge 200 is formed with four (4) tests A, B, C and D. Each test on the cartridge 200 includes a sample processing portion 212, a sample retention portion 214 and a suspension, e.g., beam 216 structurally, mechanically joining the sample retention portion 214 to the processing portion 212. The elements of the respective tests are indicated separately by the alpha designation A, B, C or D. The plurality of beams 216 shown in cantilever configuration allow the sample retention portion 214 to act as a sprung mass relative to the sample processing portion 212 and to vibrate in response to a stimulus applied to the retention structure 214 and/or the cartridge 200. Other structures, such as spring, multi-link suspensions, a semi-rigid mechanical member or members and the like capable of mechanically joining while allowing relative, dynamic movement of the sample retention portion to the sample processing portion may be used. It will be appreciated relatively small displacement, i.e., vibration of the sample is required. In certain embodiments, it may be possible to directly join the processing portion 212 and the retention structure 214 even forming them as an integral member.

The sample-processing portion 212 may include a common port feeding through a plenum or manifold or individual ports 218 through which a liquid sample 100 may be introduced into the tests of the sample processing portion 212. The ports 218 may be self-sealing such that the sample once introduced into the cartridge 200 does not flow, leak, seep, etc. from the cartridge. The ports 218 communicate with respective reservoirs or sample holding areas 220 into which the sample is initially received. The sample-processing portion 12 additionally includes, channels, vias, passages and similar structures 222; bellows or pumps 224 and valves 226 to control movement of the sample 100 or a portion thereof through the sample processing portion 212 responsive to actuation of the bellows 224 to prepare the sample 100 for testing. Application of external pneumatic pressure to the bellows 224 and operation of selected valves 226 causes the sample portion 100 to be drawn from the reservoir 220 and through and into a first passage 222' and the bellows 224. The first passage 222' may include a testing reagent, in liquid, gel, lyophilized or dried form that is mixed with the sample as it is drawn into and through the passage 222'. As described herein, reagents may be located at other locations of the cartridge 200. Cycling of the bellows 224, which may be accomplished as described by above via pulse-width modulation of the pressure and vacuum signals, allows mixing of the sample and reagent by repeated communication of the sample 100 into and through the first passage 222'. Control of the valve 226 and actuation of the bellows 224 then allows communication of the conditioned sample portion 100 through a second passage 22" to the sample retention structure 214 and sample containment structure 230. Suitable waste chambers are provided within the cartridge to ensure containment of the sample.

The cartridge 200 charged with samples 100 is then prepared and ready to be introduced into a testing apparatus to perform the tests or tests for which the cartridge is configured and to report the respective results.

Using a disposable microfluidics cartridge such as described above eliminates a previously labor-intensive process requiring skilled operators. A 4-channel cartridge, such as cartridge 200, is capable of providing four distinct test results from a single blood sample. The cartridge 200, as described, contains various dried reagents and is constructed from inexpensive injection-molded components and a multi-layer laminate. This approach simplifies running complicated assays and significantly reduces training requirements. It also reduces run-to-run and operator-to-operator variability of the instruments.

All stages of sample preparation are performed within the microfluidics cartridge, from aliquoting the original sample, reconstituting dried reagents, metering and mixing reagents into the samples, and delivering treated samples to the test areas. In accordance with herein described embodiments, suitable cartridges are configured to perform simultaneous assays with different reagents from a single whole blood sample. The automated preparation of samples provides for accurate handling of small fluid volumes and safe disposal of biological waste. Since a single standardized cartridge design can be used as the basis for a wide range of assays by tailoring the reagents applied during manufacturing, costs for the disposable cartridge are minimized.

Hemostasis Results from Thrombolastography

Standard thrombelastography (i.e., TEG5000 and CORA, also referred to throughout as CORA/TEG or CORA) provides measures of clotting time (R, enzymatic phase of coagulation), clot kinetics (a), clot strength (MA), and fibrinolysis (LY) from a single sample of whole blood. See FIG. 4.

In accordance with herein described embodiments, a cartridge, such as cartridge 200, for stroke subtype determination incorporates at least first and second tests and/or assays (collectively referred to herein as assays). A first assay may be Cora Healthcare Inc.'s cartridge-based point-of-care PlateletMapping® assay to assess a patient's hemostasis state due to enzymatic reaction (R value), uninhibited clot strength (MATHROMBIN), residual clot strength after ADP platelet receptor inhibition (MAADP), residual clot strength after TxA2 platelet receptor inhibition (MAAA), and clot lysis (LY). Since residual clot strength in the presence of ADP and TxA2 platelet receptor inhibition as well as native (uninhibited) maximum clot strength are measured, results can be obtained from samples where a subject is or is not taking antiplatelet drugs or that have ideopathic inhibition of ADP or TxA2 receptors. Because the PlateletMapping assay is able to measure both hemorrhagic and thrombotic conditions, it is able to distinguish between hemorrhagic and ischemic stroke. It will be appreciated, therefore, that other assay types adaptable to cartridge form and capable of distinguishing hemorrhagic and thrombotic conditions may be used as a first assay.

A second assay is configured to evaluate effects of other hemostasis altering therapeutics. For example, a channel or channels of the cartridge may be configured to assess the effects of novel oral anticoagulants (NOAC), which may contribute to a determination of stroke subtype.

This combination of thrombelastographic tests is unique in its ability to provide a hemostasis snapshot and to provide an indication of stroke subtype. Most stroke patients are uncommunicative when receiving emergency care, so cannot provide information regarding current medications. It is important for clinicians to know whether these patients are on hemostasis-altering drugs to make appropriate diagnosis and treatment decisions. For example, a patient may experience a hemorrhagic stroke due in part to overtreatment with either antithrombotic or anticoagulant drugs, which can be detected by suitable assays, such as the aforementioned PlateletMapping and NOAC assays, respectively.

Figure 4:
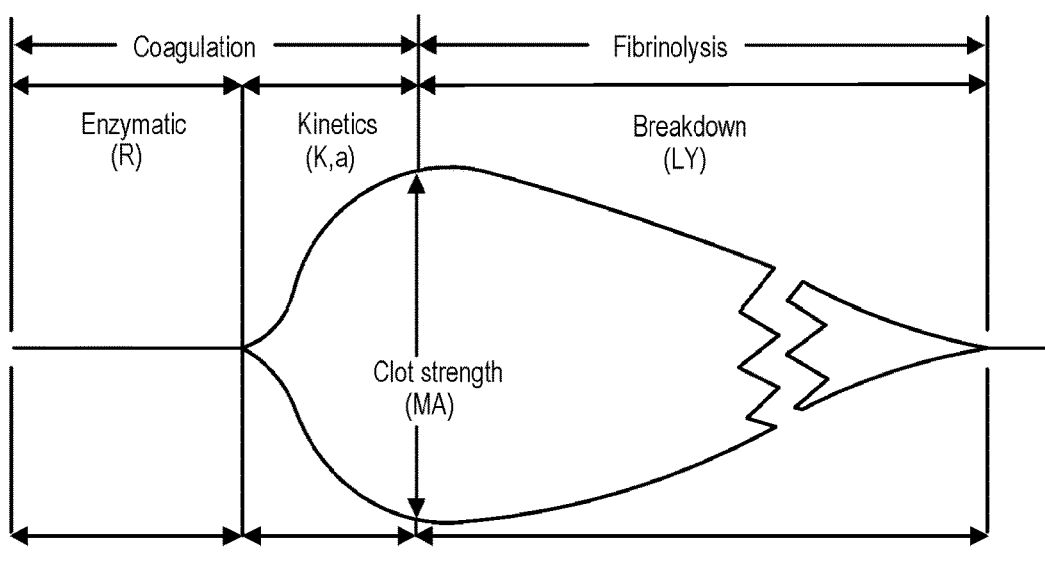
FIG. 4 is a graphic depiction of a thrombelastography waveform.

A device or devices according to the herein described embodiments are able to identify a risk for bleeding very readily through longer clotting time (R), slow clot kinetics (angle), low clot strength (MA), and high rate of lysis (LY) (see FIG. 4). At the same time, they can identify a risk for clotting through short clotting times, fast clot kinetics, high clot strength, and a low rate of lysis. The degree of risk depends on how far the parameter departs from the normal range.

Predicate Indicators

Figure 5:
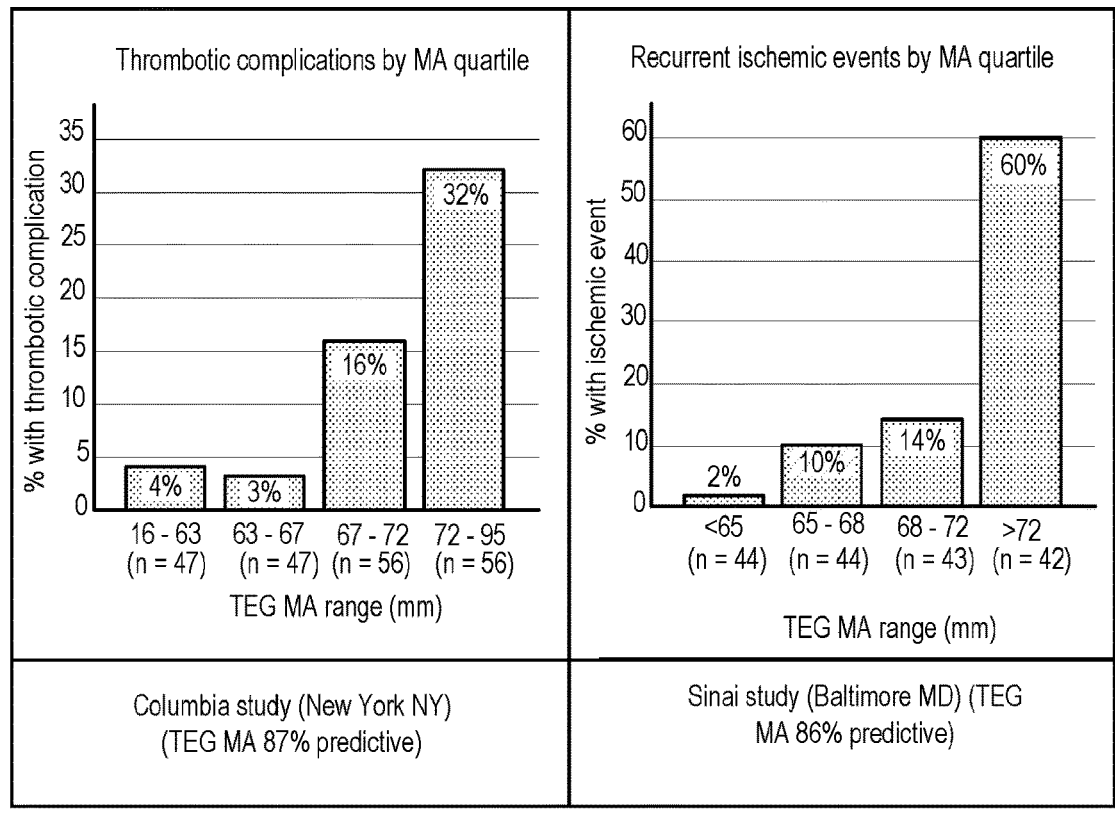
FIG. 5 displays the results of two studies that describe the quartiles used to determine ischemic and bleeding risk.

Two studies have shown how the TEG MA (clot strength) can be used to predict complications due to clotting. When the data are categorized into quartiles, the incidence of ischemic event (heart attack, stroke, pulmonary embolism, etc.) increases as the values of MA increase, as shown in FIG. 5.

Using these categories, then, physicians can assess the degree of risk a patient has for ischemic event. Risk increases as MA value increases, so a patient with MA in the $1^{st}$ quartile has a lower probability of having an ischemic event, while a patient in the $4^{th}$ quartile is at greatest risk for ischemic event, and should be treated and monitored carefully. It has also been proposed that having $MA_{ADP}$ values in the $1^{st}$ quartile may be predictive of bleeding.

Patients with implanted coronary stents, as well as others with high clot strength, are routinely prescribed a regimen of clopidogrel and aspirin therapy. A problem for physicians treating these patients is that a significant number of these on-therapy patients still have a recurrence of ischemic events, and a small but significant number have bleeding complications. Bleeding complications have been shown to be predictors of mortality in these patients, but no reliable test predictive of bleeding has been available.

Figure 6:
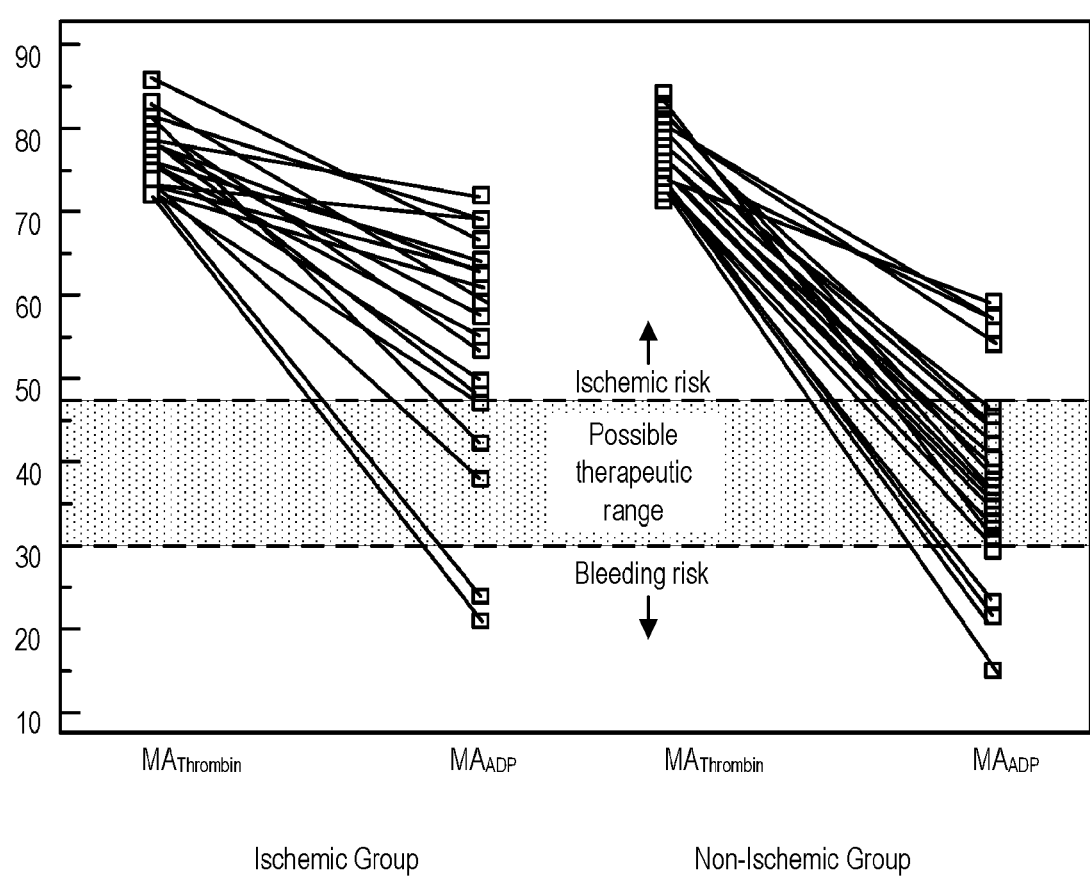
FIG. 6 compares clot strength before and after antithrombotic treatment and shows therapeutic range.

A recent article documents for the first time a therapeutic range for clopidogrel patients, identifying cut points using the TEG 5000 for both ischemic risk and bleeding risk. See FIG. 6, which shows the fourth quartile of MATHROMBIN (clot strength without treatment) with corresponding MAADP value (clot strength on treatment) for each patient. Left portion displays patients with repeated ischemic events, and right portion, without ischemic events. Dotted lines indicate cut points for ischemic and bleeding risk, and delineate a possible therapeutic range.

This very important finding can provide guidance to physicians enabling individualized dosing of clopidogrel or other new ADP inhibiting drugs, increasing dosages or changing drugs to prevent clot formation when patients are not responding adequately, as well as decreasing or discontinuing therapy to prevent bleeding for over-responders or those not requiring the drug. While there have been some findings that non-responders can be identified using other devices, because no therapeutic ranges with lower and upper limits have been established, the other devices were not able to guide dosage, especially in the area of bleeding avoidance.

It is by similar, but different and selective sample transformations and evaluation, values of these and other measurements in the stroke population may be used to determine which variables and values will be used in the stroke Index to arrive at a "hemorrhagic" vs "ischemic" classification or classification of "undetermined" when a subtype cannot be definitively identified.

The Stroke Index

The value of a stroke Index is first and foremost to reduce the time to treatment by speeding the time to diagnosis of stroke type, thus improving clinical outcomes and reducing the human and economic impact of stroke.

Many clinical studies, including those cited above, have documented various values as indicative of ischemic and hemorrhagic risk. Using those values, as well as the normal reference ranges derived from healthy individuals, a set of threshold cutoff values can be established as diagnostic for ischemic or hemorrhagic stroke.

Patient values that fall outside the cutoff values are said to be "undetermined." For illustrative purposes only, a clotting time (R) value <4 minutes and clot strength (MA)>68 mm is used to indicate an ischemic state. Similarly, R>8 minutes and MA<54 mm is used to indicate a hemorrhagic state. Further, residual clot strength ($MA_{ADP}$, $MA_{AA}$) can be used to further refine or confirm the stroke subtype in patients on antithrombotic drugs. For example, $MA_{ADP}$ values showing residual clot strength less than 50 mm indicate hemorrhagic subtype. Values that do not conform to these cutoffs are considered "undetermined." Thus, a patient presenting to the Emergency Department with R=3 minutes and MA=72 mm would be diagnosed with ischemic stroke, while a patient with R=10 minutes and MA=51 mm would be diagnosed with hemorrhagic stroke. On the other hand, stroke type is "undetermined" for a patient with R=6 minutes and MA=60 mm. Barring any contraindications, patients diagnosed with ischemic stroke could be immediately treated with antifibrinolytic drugs, hemorrhagic patients would receive clot-enhancing agents, and "undetermined" patients would follow standard hospital protocols when stroke is suspected. The NOAC assays can also assist in treatment decisions for hemorrhagic stroke patients. For example, if the assay indicates over-responsiveness to a specific NOAC, the treatment might be to administer a specific antidote to the drug.

Anecdotal retrospective evidence has shown that using the above ranges is correct 85% of the time, whether the stroke is ischemic or hemorrhagic; only 15% of strokes are classified as "undetermined."

These cutoff values are based solely on basic thrombelastographic data, and in the case of ischemic and hemorrhagic strokes may be sufficient to make a stroke subtype determination. Reducing the "undetermined" range can be achieved by incorporating additional biomarkers such as other thrombelastographic data (NOAC and PlateletMapping to test for the presence of/response to pre-existing anticoagulant and antithrombotic drugs, respectively), Rankin and NIHSS stroke scores, blood pressure, various laboratory results, patient history (e.g., previous stroke or TIA), etc. Together, all these factors may be combined to produce a single value as a Stroke Index to determine stroke type.

In cases of acute ischemic stroke, TPA thrombolytic therapy is a proven, but time-dependent intervention. Its therapeutic benefit declines with time, with no significant benefit after 4.5 hours of last known well time. Because of the importance of rapid treatment, current guidelines recommend initiation of IV TPA within 60 minutes of hospital arrival in patients without contraindications.

Using apparatus configured in accordance with the described embodiments, it is possible to arrive confidently at a stroke subtype determination: ischemic or hemorrhagic stroke, more quickly, at a lower cost, providing therapy to more patients in a shorter period of time, thereby improving clinical outcomes.

Expand Availability to Remote or Underserved Markets

With a device, such as the CORA® device, that is not affected by vibration, emergency care providers such as first responders can facilitate earlier diagnosis of acute ischemic stroke by testing in the ambulance, while in constant contact with hospital-based stroke experts. The availability of on-board stroke-targeted hemostasis testing and the stroke Index in ambulances will especially have a significant impact in areas without a nearby stroke center. Outside of major metropolitan centers, where transport to a medical facility can take an hour or more, the possibility of en route acute ischemic stroke determination and treatment with the help of telemedicine/telestroke and stroke experts guiding EMS technicians, can become a reality.

Future Potential

A foundation is laid to incorporate hemostasis data into the larger stroke domain. For example:

1. A stroke index can be used in primary prevention to manage modifiable risk markers on an individual patient basis.

2. EMS personnel can be trained to run thrombelastographic assays upon first response and/or during transport, so that information could be relayed to ED staff and other stroke team members at the destination hospital. Eventually, it might even be possible to have EMS staff administer TPA or clot-enhancing agents to certain patients, especially important in long-distance transport as may be the case outside large metropolitan medical centers and in rural, underserved locations.

3. In the hospital or point of care setting, once TPA has been administered, a blood sample can be run to determine the degree of lysis that has been achieved, administering additional amounts if needed. Lysis is not determined by body weight, as is current practice, so administering lytic drugs based on body weight is not optimum. Each patient's hemostasis state can better guide dosing, so that patients are not over- or under treated. Overdosing of TPA, in fact, could be one of the determinants of hemorrhagic conversion.

4. In determining long-term treatment for secondary prevention of recurrent stroke, using the results of thrombelastographic testing can guide proper selection of drug and dose, thereby reducing risk of over- or under treatment. This is especially important as newer and more potent drugs become available.

Although certain apparatus constructed in accordance with the teachings of the invention and methods have been described herein, the scope of coverage of this patent is not limited thereto. Generally, apparatus and methods are provided yielding for the first time an early determination of stroke subtype. In particular, a testing cartridge is configured for whole blood hemostasis testing to identify hemorrhagic and thrombotic conditions in addition to therapeutic influences providing a stroke subtype determination. The stroke subtype determination may be enhanced and improved using a Stroke index.

This patent covers all examples of the teachings of the invention fairly falling within the scope of the appended claims either literally or under the doctrine of equivalents.

We claim:

1. An apparatus to determine stroke subtype selected from acute ischemic stroke subtype and hemorrhagic stroke subtype, the system comprising:
   operably coupled a transformative apparatus, a sensor and a processor;
   the transformative apparatus being configured to excite a whole blood test sample to cause transformation of the whole blood test sample through thrombelastography;
   the sensor being configured relative to the transformative apparatus to measure a physical characteristic of the whole blood test sample during transformation and to provide data representative of the physical characteristic; and
   the processor being configured to control operation of the transformative apparatus to effect transformation of the whole blood test sample and to receive the data, the processor being further configured to determine a stroke index based at least on the data and to provide a stroke subtype indication based on a relationship of the stroke index to a set of cutoff values, wherein the stroke subtype indication is one of ischemic stroke subtype and hemorrhagic stroke subtype.

2. The apparatus of claim 1, wherein the transformative apparatus comprises a cartridge having first and second channels, the first and second channels corresponding to first and second transformations to be conducted on the whole blood test sample, respectively.

3. The apparatus of claim 2, wherein the first channel is configured according to a first assay and the second change is configured according to a second assay, different than the first assay.

4. The apparatus of claim 1, wherein the physical characteristic comprises at least one of a clotting time and a clot strength.

5. The apparatus of claim 1, wherein the set of cutoff values comprise a reference clotting time and a reference clot strength.

6. The apparatus of claim 1, wherein the set of cutoff values comprise a first reference clotting time and a first reference clot strength and a second reference clotting time different than the first reference clotting time and a second reference clot strength different than the first reference clot strength.

7. The apparatus of claim 5, wherein the set of cutoff values further comprise at least one biomarker.

8. The apparatus of claim 1, wherein the stroke subtype indication further comprises undetermined.

9. The apparatus of claim 1, wherein the physical characteristic comprises a resonant vibration frequency.

10. The apparatus of claim 1, further comprising a cartridge to determine stroke subtype selected from ischemic stroke subtype and hemorrhagic stroke subtype, the cartridge configured to be operably coupled to the transformative apparatus and comprises: a sample preparation portion including a fluid processing structure; a sample testing portion including a sample retention structure, the sample testing portion being coupled to the sample preparation portion via a fluidic passage providing fluid communication between the fluid processing portion and the sample retention structure; the sample retention structure supporting the whole blood test sample to be tested such that the whole blood test sample may be excited to resonant vibration responsive to an excitation applied to the cartridge by the transformative apparatus and observed by the sensor.

* * * * *